United States Patent [19]
Shen

[11] Patent Number: 5,851,384
[45] Date of Patent: Dec. 22, 1998

[54] APPARATUS FOR AUTOMATICALLY DELIVERING HEMODIALYSIS SOLUTION TO A PLURALITY OF HEMODIALYSIS MACHINES

[76] Inventor: Tsong-Nan Shen, No. 4, Alley 25, Lane 103, Shih-Chien St., Tainan City, Taiwan

[21] Appl. No.: 666,212

[22] Filed: Jun. 20, 1996

[51] Int. Cl.[6] .......................... B01D 17/12; B01D 35/02; F17D 3/00
[52] U.S. Cl. .......................... 210/104; 137/395; 137/565; 137/572; 210/96.2; 210/257.2; 422/106
[58] Field of Search ............... 210/86, 96.2, 97, 210/104, 134, 135, 143, 257.2, 248, 258, 321.69, 321.71, 636, 646, 647, 257.1; 604/4–6; 137/572, 87.02, 109, 115.01, 115.02, 255, 395, 565; 422/106, 107

[56] References Cited

U.S. PATENT DOCUMENTS

| | | | |
|---|---|---|---|
| 3,352,779 | 11/1967 | Austin et al. | 210/321.71 |
| 3,441,136 | 4/1969 | Serfass et al. | 210/96.2 |
| 4,137,168 | 1/1979 | Perrot | 210/104 |
| 4,444,597 | 4/1984 | Gortz et al. | 210/646 |

*Primary Examiner*—Joseph W. Drodge
*Attorney, Agent, or Firm*—Foley & Lardner

[57] ABSTRACT

An apparatus for automatically delivering hemodialysis solution to a plurality of hemodialysis machines includes a plurality of supply tanks adapted to be fluidly communicated with a corresponding one of the hemodialysis machines. Each of the supply tanks has a bottom portion provided with a connecting port. A main tank contains the hemodialysis solution therein and is formed with an outlet port. A solution delivery system includes a main delivery pipe which has an inlet section connected to the outlet port of the main tank and provided with an electromagnetic delivery control valve and a delivery pump, and a plurality of main branch pipes. Each of the main branch pipes has an input portion connected fluidly to the main delivery pipe and an output portion connected fluidly to the connecting port of a respective one of the supply tanks. Each of the main branch pipes is provided with an electromagnetic main branch valve. A monitoring device is connected electrically to the delivery control valve, the delivery pump and the main branch valves. The monitoring device controls the delivery control valve, the delivery pump and the main branch valves to fill up the supply tanks.

12 Claims, 20 Drawing Sheets

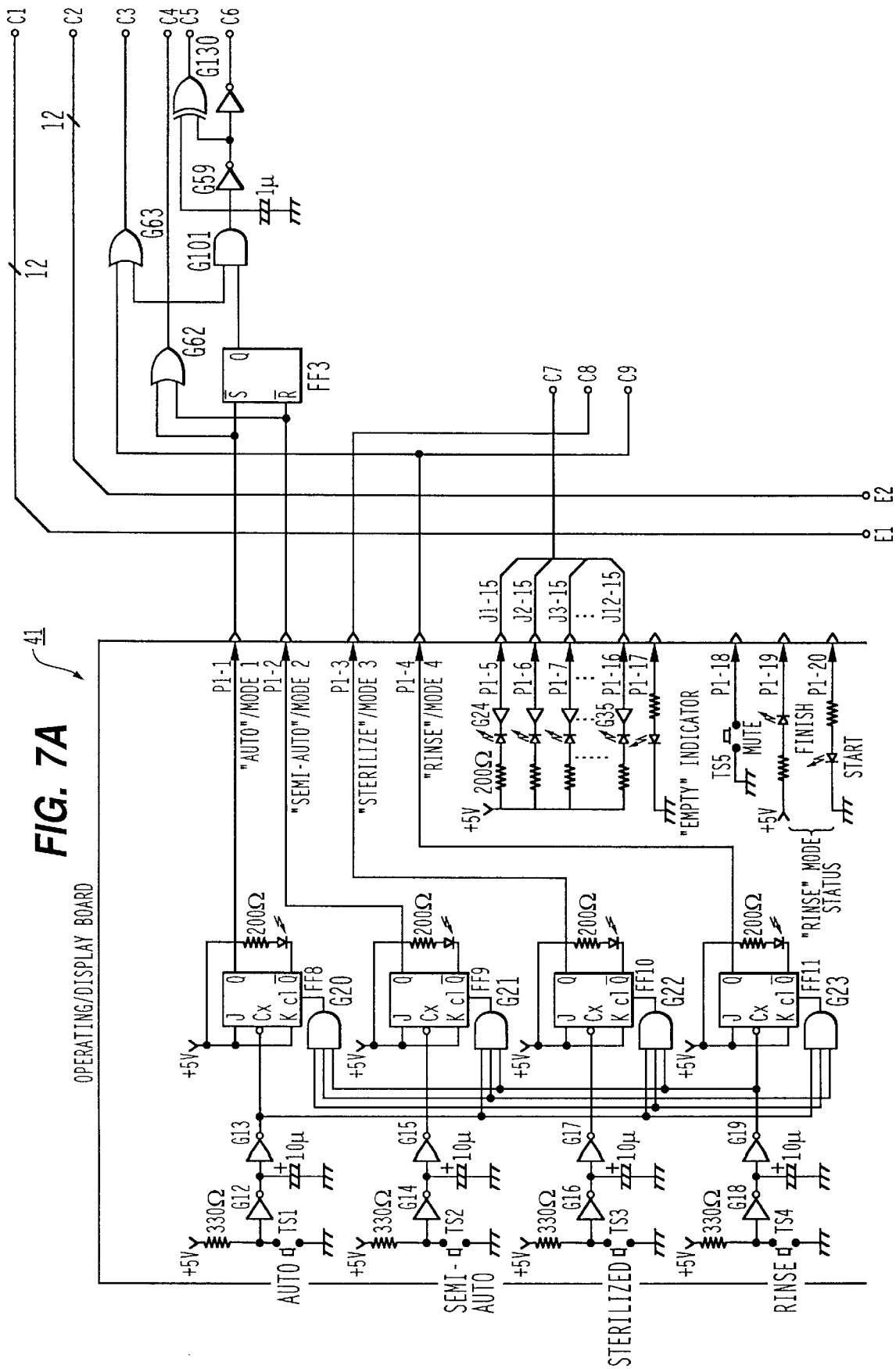

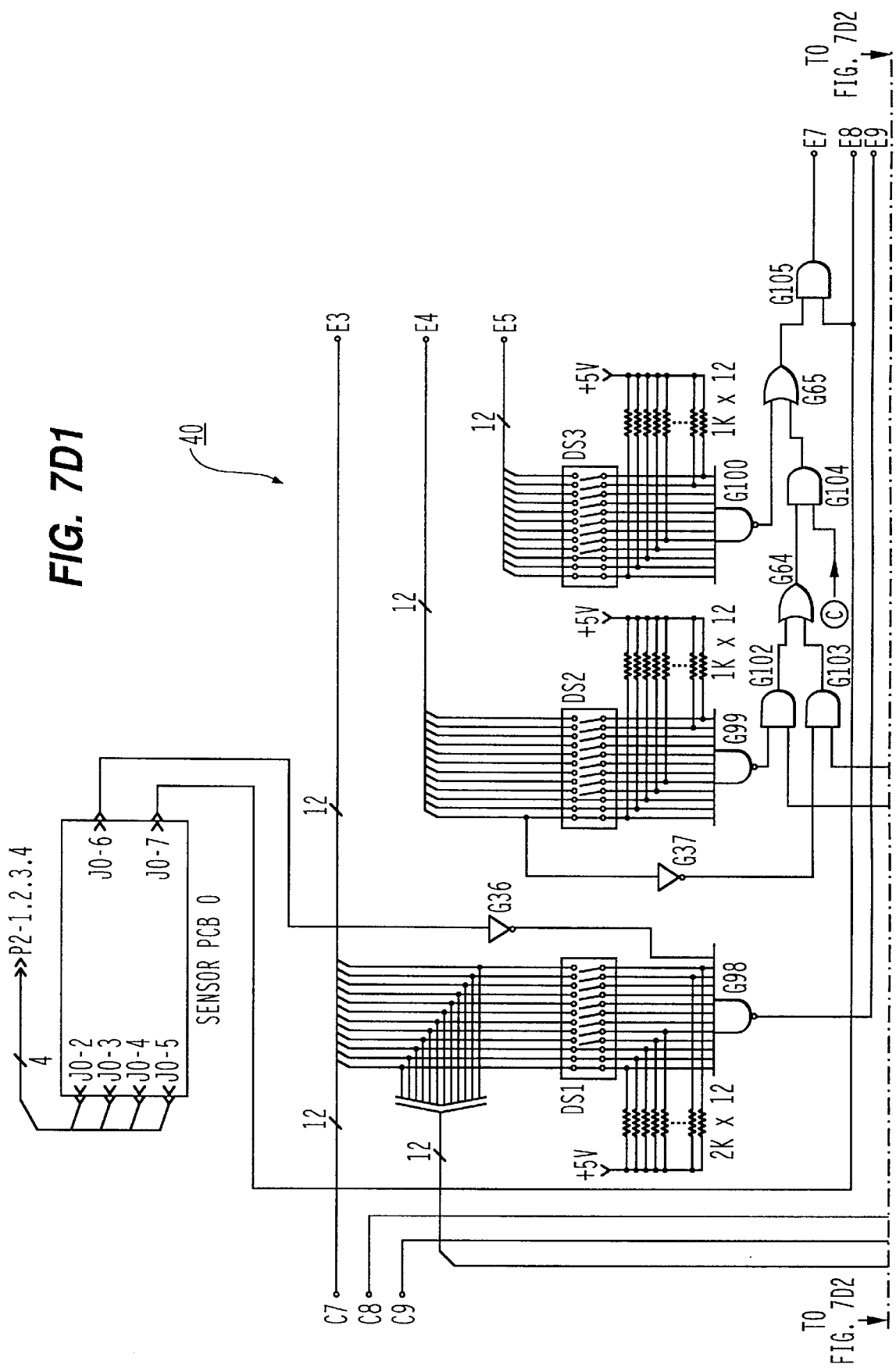
FIG. 7D1

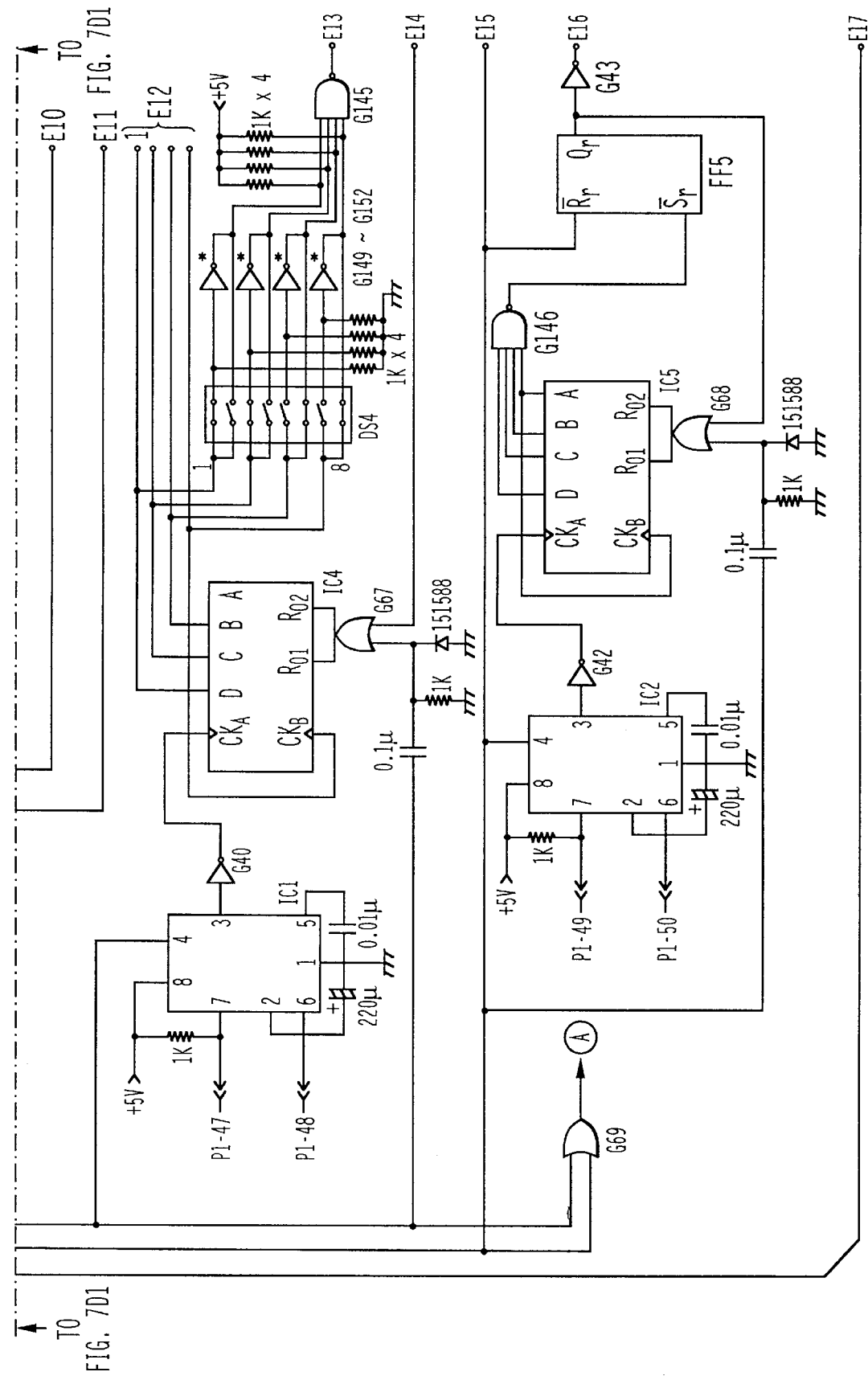
FIG. 7D2

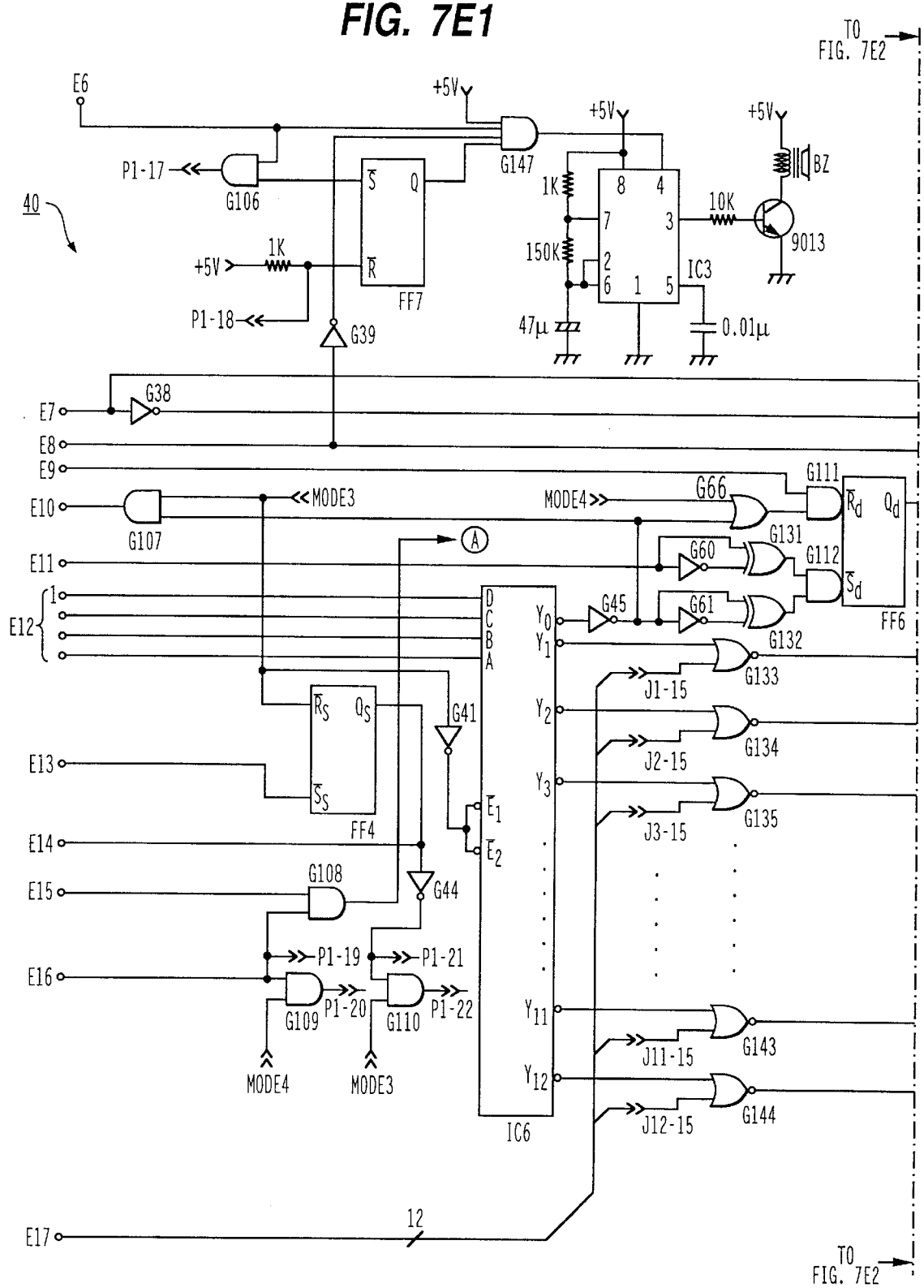
FIG. 7E1

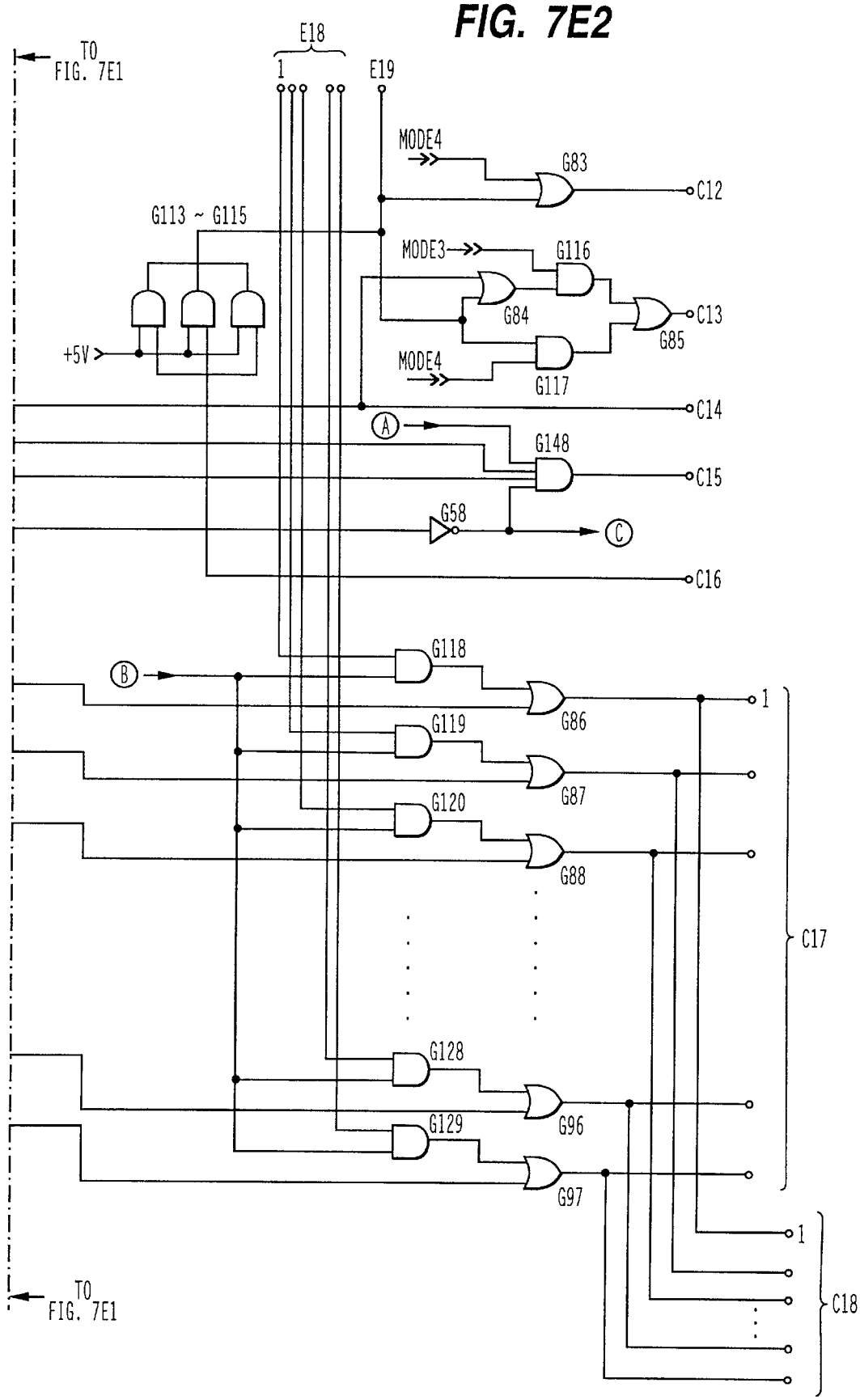
FIG. 7E2

5,851,384

APPARATUS FOR AUTOMATICALLY DELIVERING HEMODIALYSIS SOLUTION TO A PLURALITY OF HEMODIALYSIS MACHINES

BACKGROUND OF THE INVENTION

1. Field of the Invention

The invention relates to a delivering apparatus, more particularly to an apparatus for automatically delivering hemodialysis solution to a plurality of hemodialysis machines.

2. Description of the Related Art

Presently, the delivery of hemodialysis solution to hemodialysis machines in a hospital ward is done manually. Before treatment in the hospital ward commences, a nurse calculates the required amount of hemodialysis solution for each patient and goes to the supply room to retrieve the hemodialysis solution. Usually, the amount of hemodialysis solution should be sufficient to conduct about four hours of treatment for each patient. During treatment, monitoring of the remaining amount of hemodialysis solution is needed for each patient to ensure that an adequate amount of the hemodialysis solution remains. When the remaining amount of hemodialysis solution is insufficient, replenishing of the hemodialysis solution must be performed to ensure proper operation of the hemodialysis machine. Although the delivery of hemodialysis solution during treatment and the monitoring of the remaining amount of hemodialysis solution seem simple, these labor-intensive and time consuming operations increase in complexity as the number of patients in the hospital ward increases.

SUMMARY OF THE INVENTION

Therefore, the object of the present invention is to provide an apparatus for automatically delivering hemodialysis solution to a plurality of hemodialysis machines so as to overcome the aforementioned drawback of the prior art.

Accordingly, the apparatus of the present invention is capable of automatically delivering hemodialysis solution to a plurality of hemodialysis machines and comprises:

a plurality of supply tanks adapted to be fluidly communicated with a corresponding one of the hemodialysis machines, each of the supply tanks having a bottom portion provided with a connecting port, each of the supply tanks being further provided with an upper level sensing unit for detecting whether the supply tank is full, and a lower level sensing unit for detecting whether the supply tank is empty;

a main tank for containing the hemodialysis solution therein, the main tank being formed with an outlet port;

a solution delivery system including a main delivery pipe which has an inlet section connected to the outlet port of the main tank and provided with an electromagnetic delivery control valve and a delivery pump, and a plurality of main branch pipes, each of the main branch pipes having an input portion connected fluidly to the main delivery pipe and an output portion connected fluidly to the connecting port of a respective one of the supply tanks, each of the main branch pipes being provided with an electromagnetic main branch valve; and a monitoring device connected electrically to the upper and lower level sensing units, the delivery control valve, the delivery pump and the main branch valves, the monitoring device being operable in an automatic mode, wherein the monitoring device activates and deactivates the delivery control valve, the delivery pump and the main branch valves to fill up the supply tanks.

BRIEF DESCRIPTION OF THE DRAWINGS

Other features and advantages of the present invention will become apparent in the following detailed description of the preferred embodiment, with reference to the accompanying drawings, of which.

DETAILED DESCRIPTION OF THE PREFERRED EMBODIMENT

Figure 1:
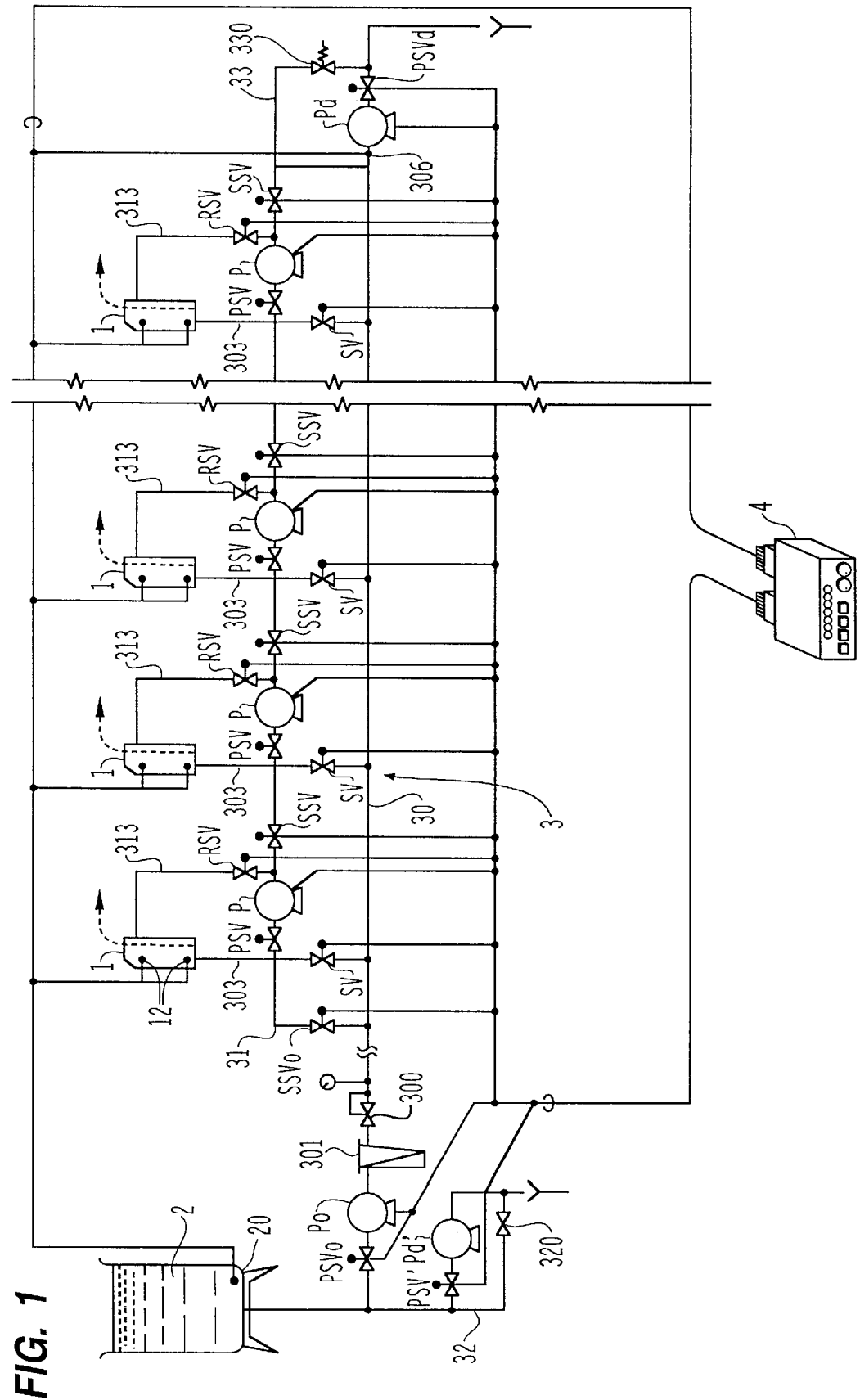
FIG. 1 is a schematic view of the preferred embodiment of an apparatus according to the present invention.

Referring to FIG. 1, the preferred embodiment of an apparatus according to the present invention is shown to comprise a plurality of supply tanks 1, a main tank 2, a solution delivery system 3, and a monitoring device 4.

Figure 2:
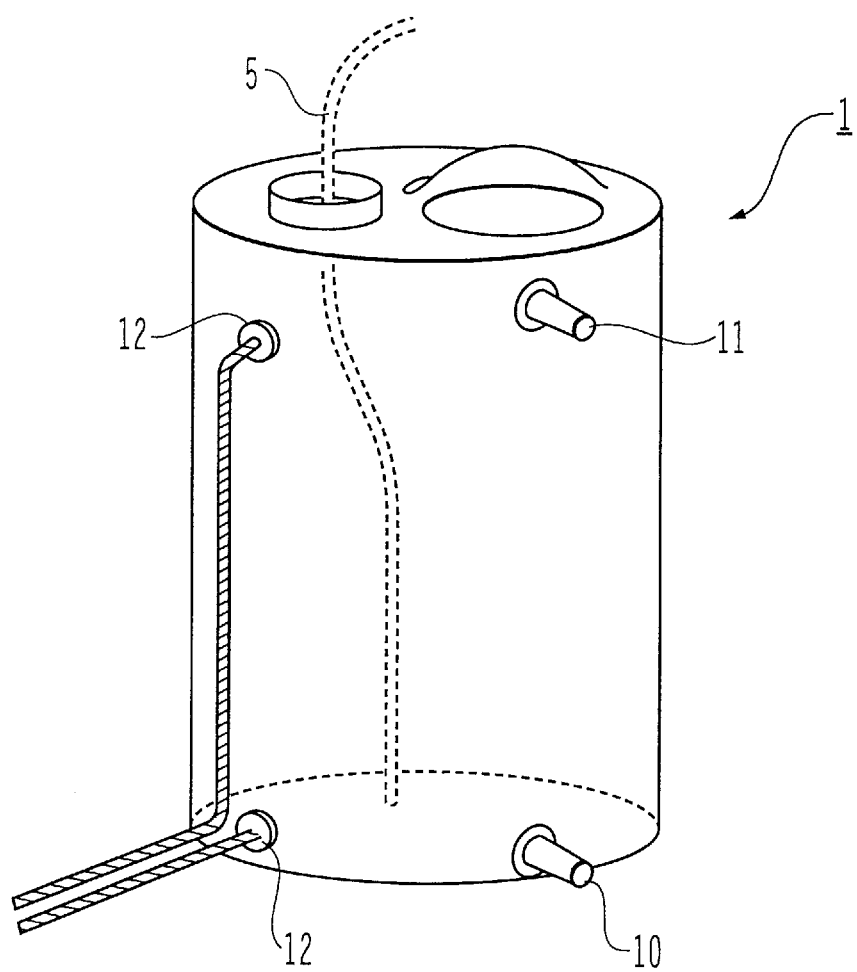
FIG. 2 is a perspective view of a supply tank of the preferred embodiment.

As shown in FIG. 2, each of the supply tanks 1 is used to contain the hemodialysis solution that is to be supplied to a corresponding hemodialysis machine and has a bottom portion provided with a connecting port 10 and a top portion provided with a circulating port 11. The top and bottom portions of each supply tank 1 are further provided with a respective level sensing unit 12 for detecting whether the supply tank 1 is full or empty. In this embodiment, the level sensing unit 12 is constituted by two conductive probes (not shown). Referring once more to FIG. 1, the main tank 2 contains the hemodialysis solution that is to be delivered to each of the supply tanks 1, and is provided with an outlet port and a liquid sensing unit 20 at a bottom portion.

The solution delivery system 3 includes a main delivery pipe 30. The outlet port of the main tank 2, an electromagnetic delivery control valve PSVo, a delivery pump Po, a filter unit 301 and a pressure regulator 300 are connected in series to an inlet section of the main delivery pipe 30. A residual liquid sensing unit 306, a drain pump Pd and an electromagnetic draining control valve PSVd are provided on a distal section of the main delivery pipe 30. Each of a plurality of main branch pipes 303 has an input portion connected fluidly to the main delivery pipe 30 and an output portion connected fluidly to the connecting port 10 of a respective one of the supply tanks 1. Each of the main branch pipes 303 is provided with an electromagnetic main branch valve SV. A secondary pipe 31 is connected fluidly to the inlet section of the main delivery pipe 30 and to the outlet portion of each of the main branch pipes 303. The secondary pipe 31 has an inlet portion provided with an electromagnetic sterilization entrance valve SSVo for controlling the path of the sterilizing solution. In order to transmit sterilizing solution, the secondary pipe 31 is further equipped with a plurality of electromagnetic mediating pump control valves PSV, a plurality of mediating pumps P and a plurality of transmission control valves SSV. Preferably, the secondary pipe 31 has a plurality of pipe sections disposed between a respective pair of the main branch pipes 303 and provided with one of the mediating pump control valves PSV, one of the mediating pumps P and one of the transmission control valves SSV. Each of the mediating pump control valves PSV is used to shut down liquid flow therethrough so that each of the supply tanks 1 may be filled with hemodialysis solution via the main branch pipes 303, respectively. Since the flow of liquid to each of the mediating pumps P is controlled by the corresponding one of the control valves PSV, the mediating pumps P and the control valves PSV are activated or deactivated at the same time. In addition, for the purpose of forming a circulating path for rinsing, each of a plurality of secondary branch pipes 313 is connected fluidly to the secondary pipe 31 and to the circulating port 11 of a respective one of the supply tanks 1. Each of the secondary branch pipes 313 is further provided with an electromagnetic circulation control valve RSV. Both the main delivery pipe 30 and the main tank 2 are connected fluidly to a drain pipe 32 which has a drain pump Pd' and an electromagnetic drain valve PSV'. The drain pipe 32 is further provided with a manually operated bypass valve 320. Moreover, the main delivery pipe 30 has a terminal portion provided with a bypass pipe 33 to connect the main delivery pipe 30 and a last one of the transmission control valves SSV. The bypass pipe 33 is provided with a pressure relief valve 330 for releasing excess pressure in the main delivery pipe 30.

Figure 3:
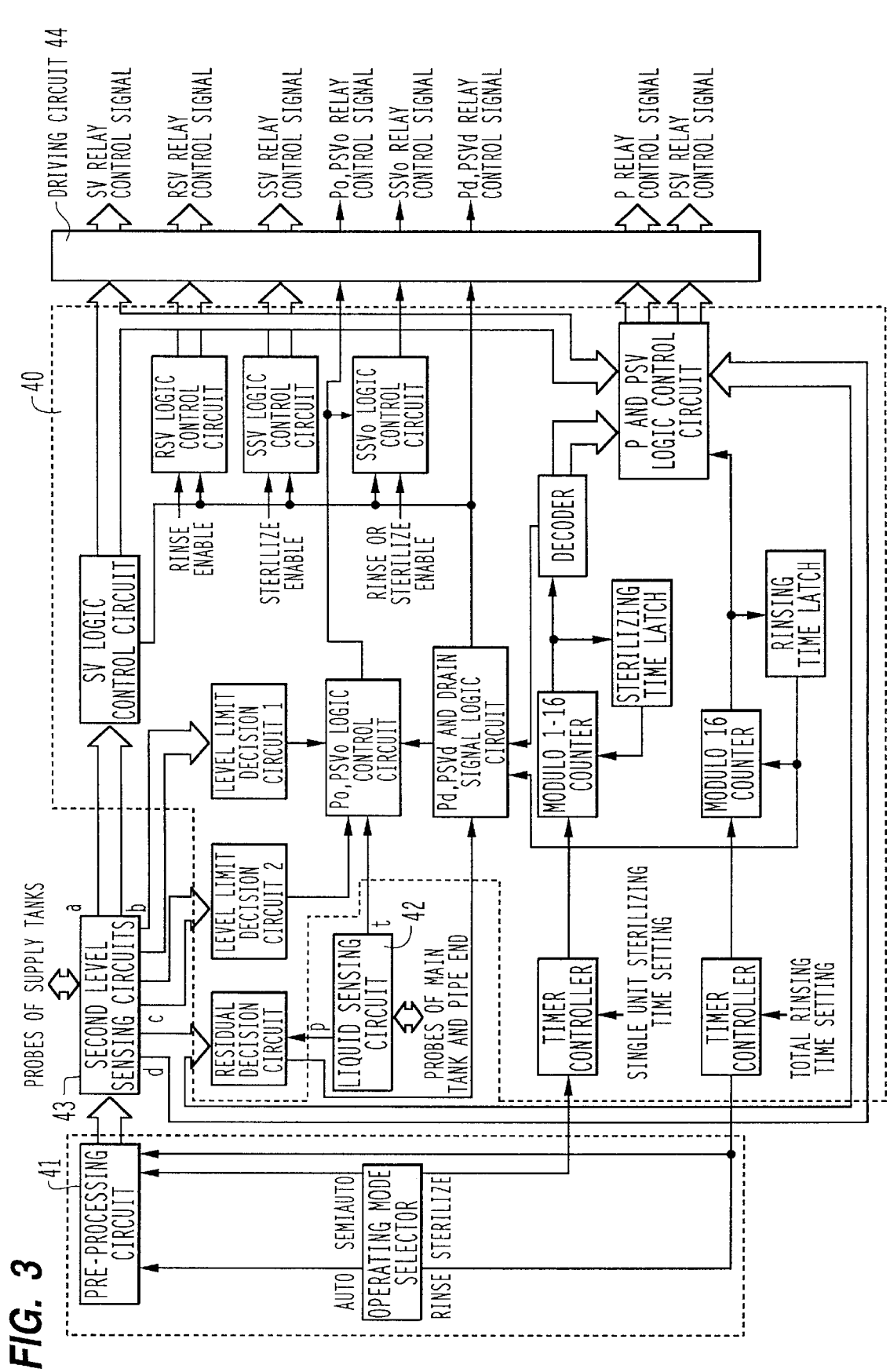
FIG. 3 is a schematic circuit block diagram of a monitoring device of the preferred embodiment.

The monitoring device 4 serves to monitor and control the delivery of hemodialysis solution from the main tank 2 to the supply tanks 1. As shown in FIG. 3, the monitoring device 4 includes a central control circuit 40, a control panel 41, a liquid sensing circuit 42, a plurality of level sensing circuits 43 and a driving circuit 44. The control panel 41, the liquid and level sensing circuits 42, 43, and the driving circuit 44 are connected electrically to the central control circuit 40.

Figure 4:
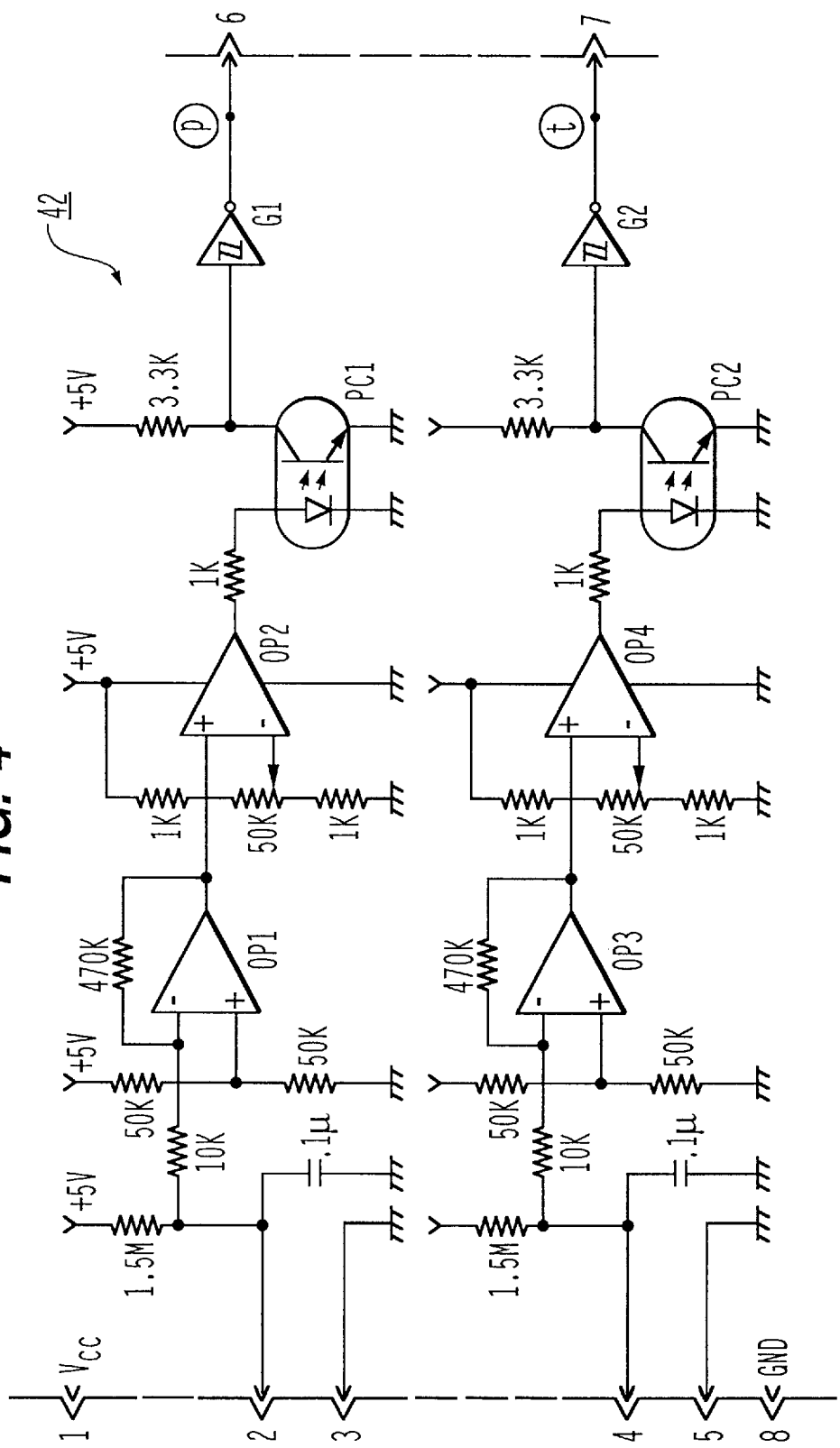
FIG. 4 is a schematic electrical circuit diagram of a liquid sensing circuit of the preferred embodiment.

Referring to FIG. 4, the liquid sensing circuit 42 includes two sets of liquid sensors. Input pins 2 and 3 of the liquid sensing circuit 42 are connected electrically to the liquid sensing unit 20 on the bottom portion of the main tank 2. Input pins 4 and 5 of the liquid sensing circuit 42 are connected electrically to the liquid sensing unit 306 on the distal section of the main delivery pipe 30. Each of the liquid sensors has a variable voltage input due to the varying resistance between the conductive probes of the corresponding one of the liquid sensing units 20, 306. The variable voltage input is amplified and compared with a reference voltage by an operational amplifier unit OP1–OP4 to detect the remaining amount of solution in the main tank 2 and the main delivery pipe 30. The operation of the liquid sensing circuit 42 will now be described with reference to input pins 2 and 3. When the conductive probes of the liquid sensing unit 20 are not in contact with the solution in the main tank 2, i.e. the main tank 2 is empty, an infinite resistance (open circuit) is present across the input pins 2 and 3 such that the output of the OP2 amplifier and output pin 6 present a low logic signal. When both of the conductive probes of the liquid sensing unit 20 are in contact with the solution in the main tank 2, the resistivity of the solution generates a resistance across the input pins 2 and 3. Since the input pins 2 and 3 form part of a voltage divider circuit, a high logic signal corresponding to the remaining solution in the main tank 2 is thereby presented at output pin 6. Thus, the central control circuit 40 is able to determine whether the main tank 2 is empty and whether residual solution is present in the main delivery pipe 30.

Figure 5:
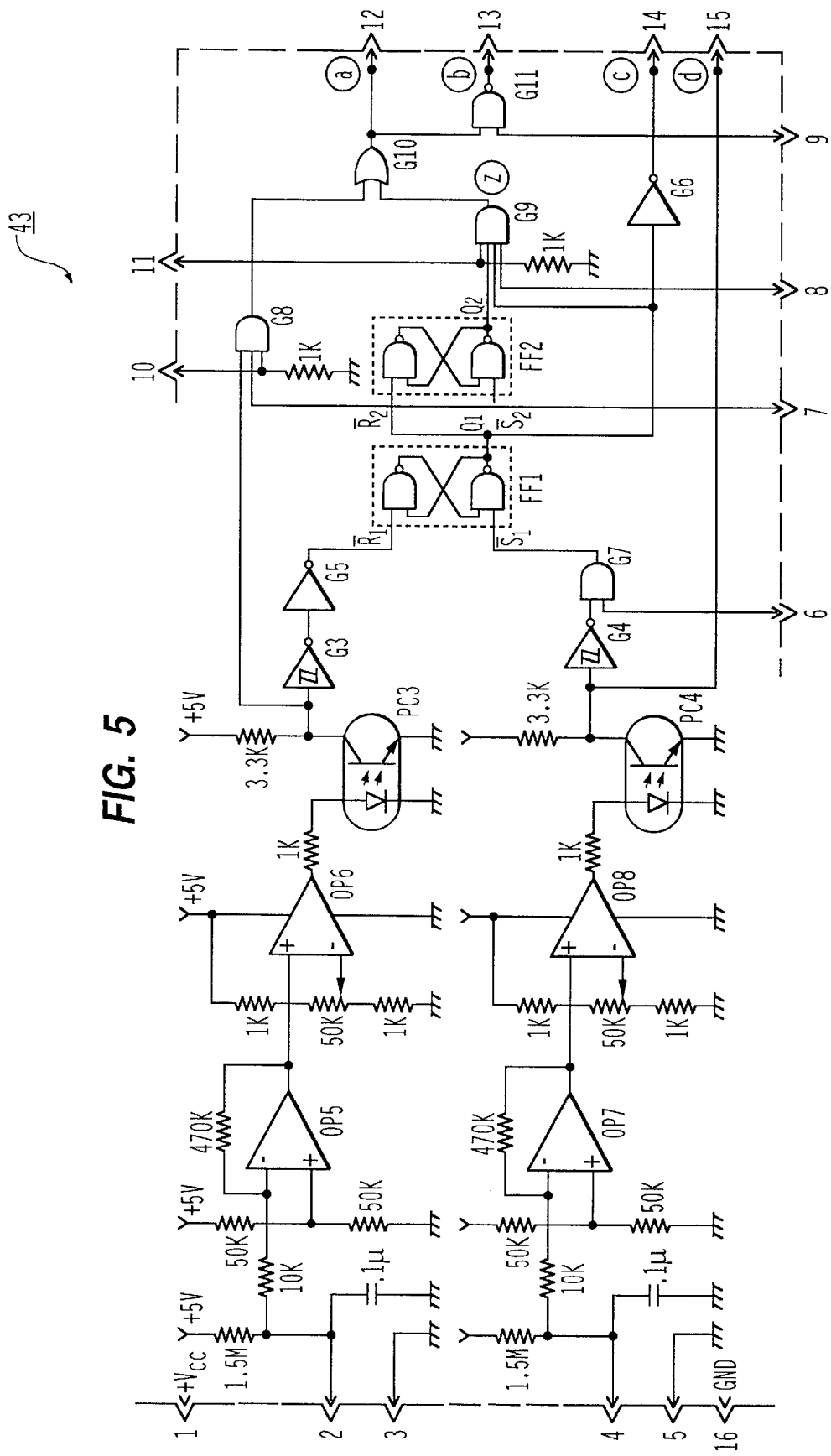
FIG. 5 is a schematic electrical circuit diagram of a level sensing circuit of the preferred embodiment.

Referring to FIG. 5, each of the level sensing circuits 43 also includes two sets of liquid sensors similar to those of the liquid sensing circuit 42, and a logic circuit for generating control signals that are used in the delivery of hemodialysis solution to the supply tanks 1. Each of the level sensing circuits 43 is capable of detecting whether the respective one of the supply tanks 1 is empty or full, and has two sets of input pins connected to the conductive probes of the level sensing units 12 at the top and bottom portions of the respective supply tank 1. The signals of the level sensing units 12 are fed to a flip-flop set FF1, FF2 of the logic circuit, and the resulting outputs are latched to control operation of the main branch valves SV. The central control circuit 40 generates the appropriate control signals upon determining the condition in each of the supply tanks 1, as will be described in greater detail in the succeeding paragraphs.

Figure 6:
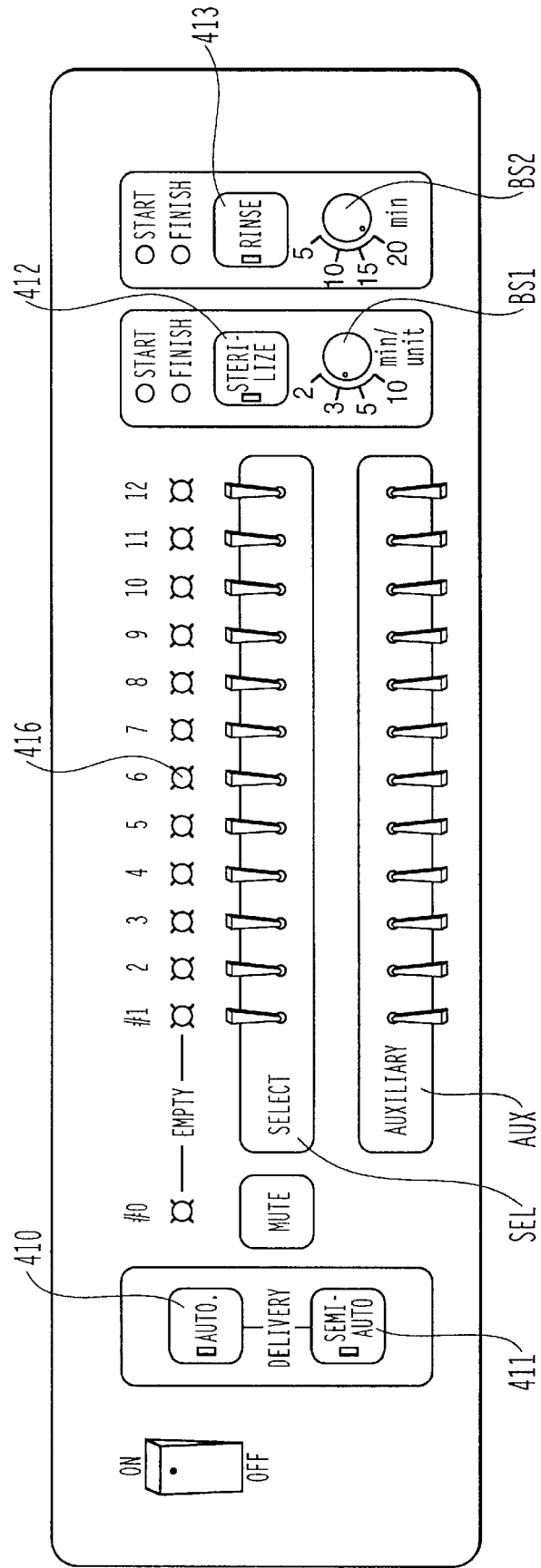
FIG. 6 is a schematic view of a control panel of the monitoring device of the preferred embodiment.
Figure 7B:
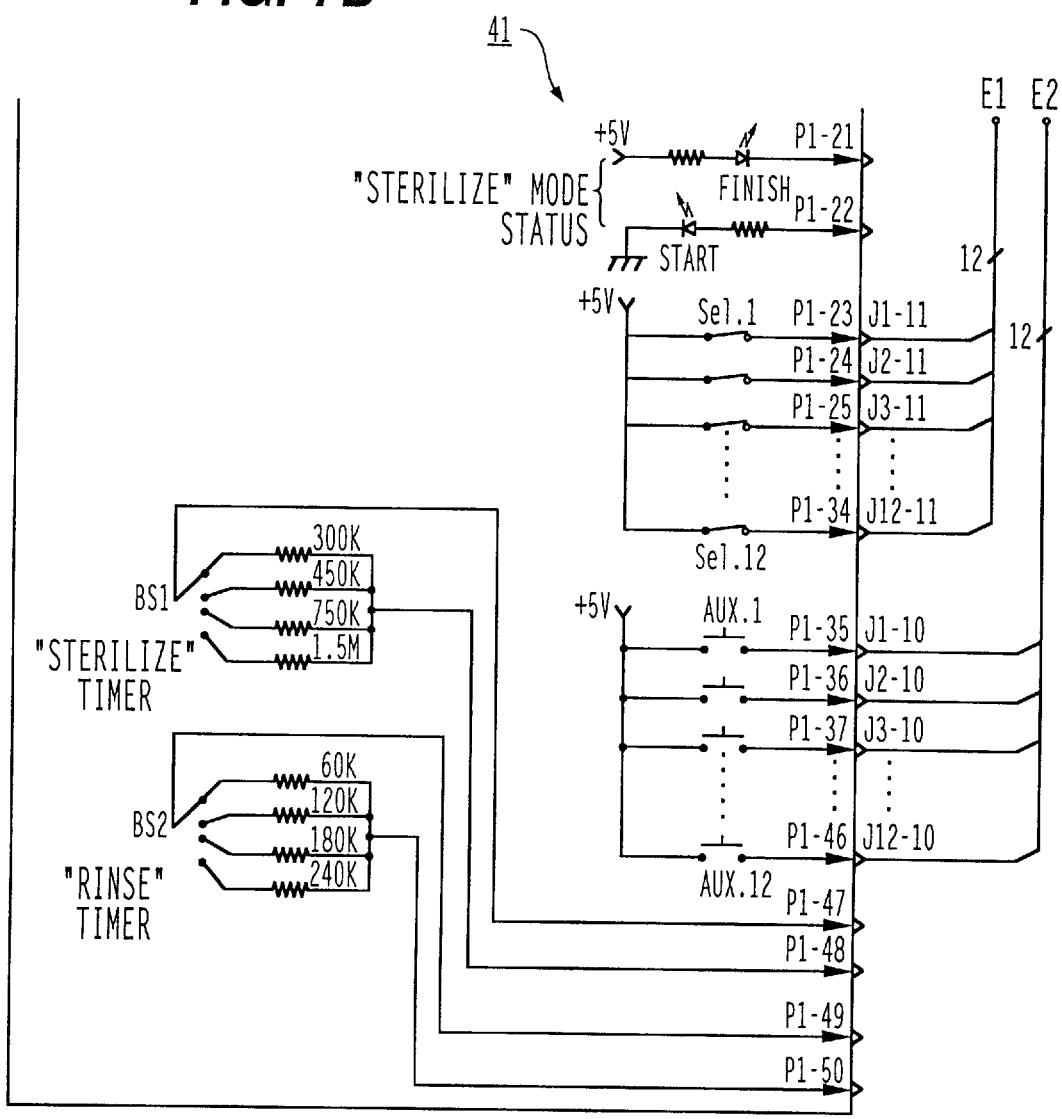
FIGS. 7A, 7B, 7C, 7D (which comprises 7D1 and 7D2), 7E (which comprises 7E1 and 7E2), and 7F are schematic electrical circuit diagrams of the monitoring device of the preferred embodiment.

Referring to FIGS. 6, 7A and 7B, the control panel 41 is operable so as to set the operating mode of the central control circuit 40. The control panel 41 includes four functions keys 410, 411, 412, 413, which are defined as automatic, semi-automatic, sterilizing and rinsing function keys, respectively. The control panel 41 further includes two sets of switches SEL, AUX. The switches SEL are operated to select the hemodialysis machines (not shown) to be used during treatment and the supply tanks 1 corresponding thereto. The switches AUX are operated during the semi-automatic mode so as to select manually which ones of the supply tanks 1 are to be replenished, as will be described in greater detail in the succeeding paragraphs. The control panel 41 additionally includes a set of light emitting diode (LED) indicators 416 for indicating which ones of the main tank 2 and the supply tanks 1 are empty, and two multi-position switches BS1, BS2 for setting the sterilizing and rinsing times.

Figure 7C:
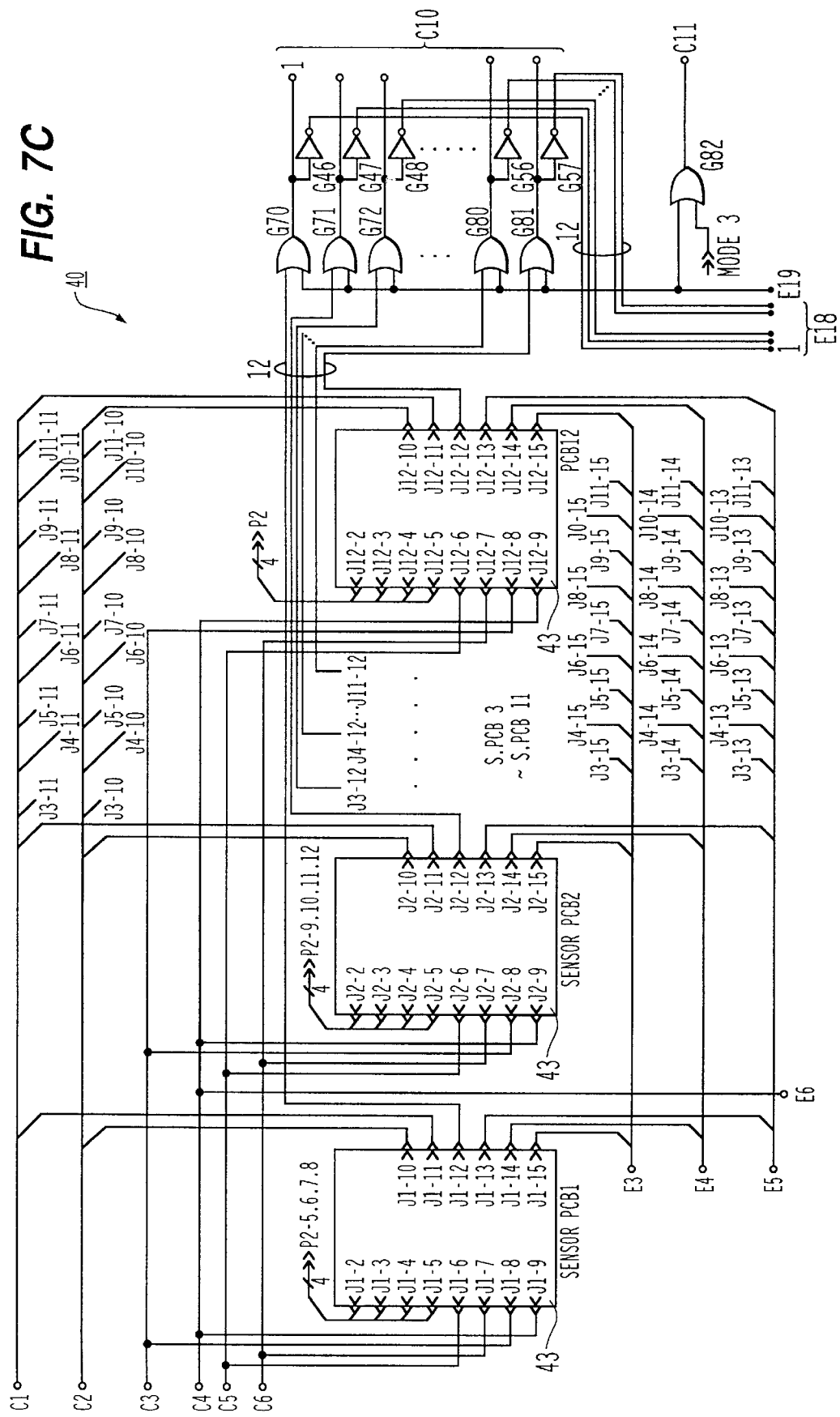

As shown in FIGS. 7C, 7D and 7E, the central control circuit 40 is the heart of the monitoring device 4 and receives the outputs of the liquid and level sensing circuits 42, 43. In this embodiment, the central control circuit 40 is constituted by flip-flops, counters, decoders and logic gates to perform the required procedures during automatic, semi-automatic, sterilizing and rinsing operations of the preferred embodiment.

Figure 7F:
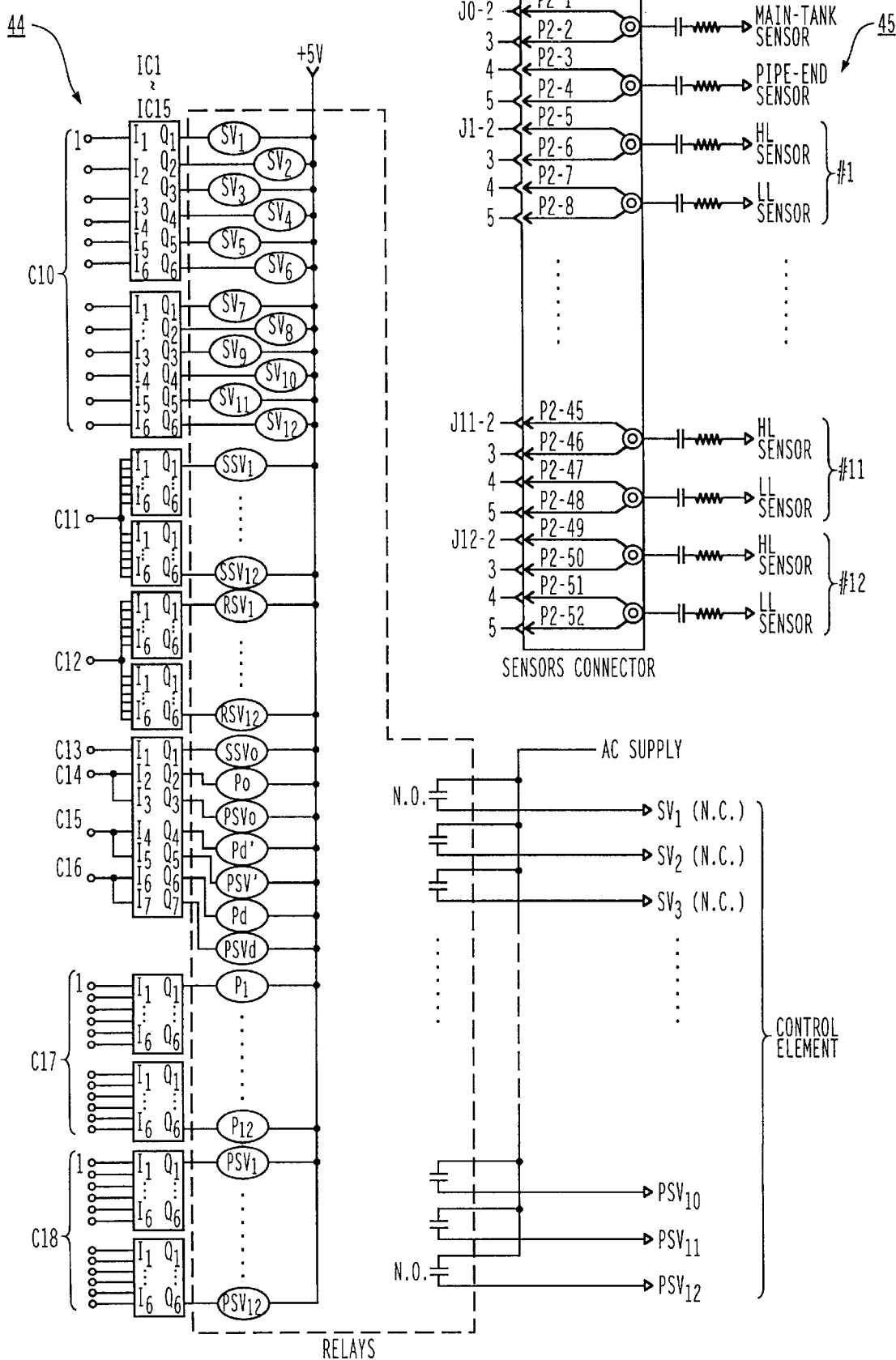

As shown in FIG. 7F, the driving circuit 44 receives a plurality of control signals from the output ports of the central control circuit 40 so as to drive the control relays that are adapted to activate or deactivate a corresponding control element of the electromagnetic valves SV, SSVo, PSVo, PSV', PSVd, PSV, SSV, RSV and the pumps Po, Pd, Pd', P. The monitoring device 4 is additionally provided with a sensor connecting device 45 for connection with the various sensing units 12, 20, 306.

In the present embodiment, the monitoring device 4 is capable of controlling the delivery of hemodialysis solution to twelve supply tanks 1 by setting the switch DS4 (see FIG. 7D) and of monitoring the remaining hemodialysis solution in the supply tanks 1. In use, the switch DS4 is set in accordance with the actual number of hemodialysis machines that are installed in the site.

Each of the supply tanks 1 is to be installed near a corresponding hemodialysis machine (not shown) in the hemodialysis ward. A suction tube 5 (see FIG. 2) extends from an internal pump of the hemodialysis machine and into the supply tank 1 so as to communicate the hemodialysis solution to the corresponding hemodialysis machine. In the present embodiment, the apparatus is operable in the automatic and semi-automatic modes to provide greater flexibility in use and to permit adjustments in the amount of hemodialysis solution that is supplied to each patient. The apparatus is further operable in the sterilizing and rinsing modes in order to minimize the risk of contamination. In addition, before the apparatus of the preferred embodiment is operated in the desired mode, the main tank 2 should be initially filled with the required hemodialysis solution, sterilizing solution or reverse osmosis water for rinsing.

Before use, the control panel 41 is operated so as to cause the central control circuit 40 to operate in the desired mode.

Figure 8:
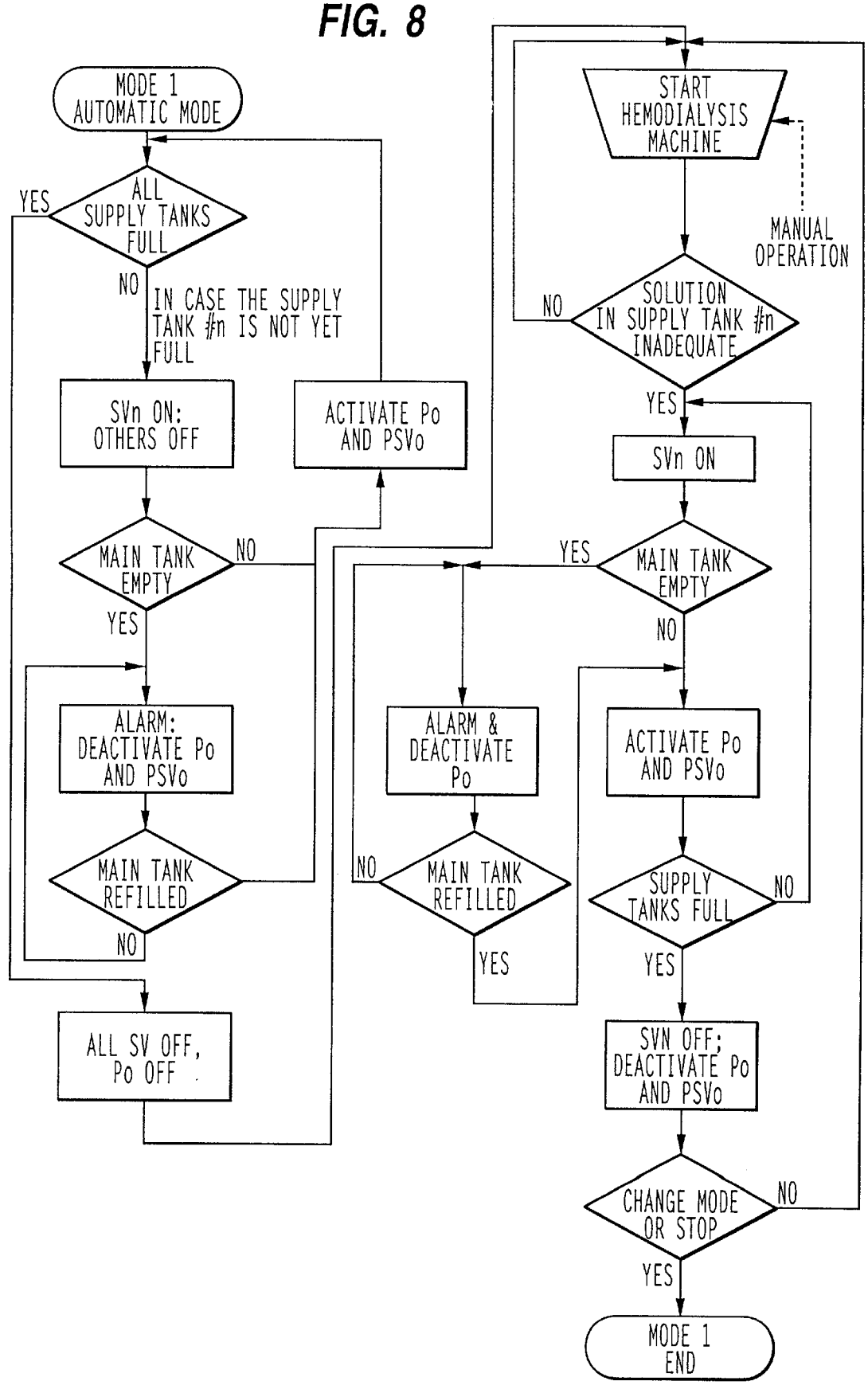
FIG. 8 is a flowchart illustrating the operation of the preferred embodiment in an automatic mode.

FIG. 8 is a flowchart which illustrates the operation of the preferred embodiment in the automatic mode. Initially, a nurse estimates the total required amount of hemodialysis solution and supplies the same to the main tank 2 manually or with the use of a pump. When automatic operation of the preferred embodiment is initiated, the monitoring device 4 determines whether there is an adequate amount of hemodialysis solution in each of the supply tanks 1. When the amount of solution in any of the supply tanks 1 is inadequate, i.e. an infinite resistance is present at the level sensing unit 12 at the top portion of one of the supply tanks 1, the monitoring device 4 opens the electromagnetic valve SV of the main branch pipe 303 that is associated with the inadequate one of the supply tanks 1 and activates the delivery pump Po and the electromagnetic valve PSVo. The hemodialysis solution flows from the main tank 2, the electromagnetic valve PSVo, the delivery pump Po, the electromagnetic valve SV, and into the supply tank 1 at this time, as shown in FIG. 1. When the particular supply tank 1 is full, i.e. the hemodialysis solution in the supply tank 1 reaches the upper level sensing unit 12, the monitoring device 4 closes the corresponding electromagnetic valve SV to stop the delivery of hemodialysis solution to the supply tank 1. After all of the supply tanks 1 have been filled, the monitoring device 4 deactivates the delivery pump Po and the electromagnetic valve PSVo. At this time, each of the supply tanks 1 is capable of providing hemodialysis solution for a treatment period of about four hours. The monitoring device 4 repeats the aforementioned delivering operation whenever the level of hemodialysis solution in any of the supply tanks 1 drops below the lower one of the level sensing units 12.

Figure 9A:
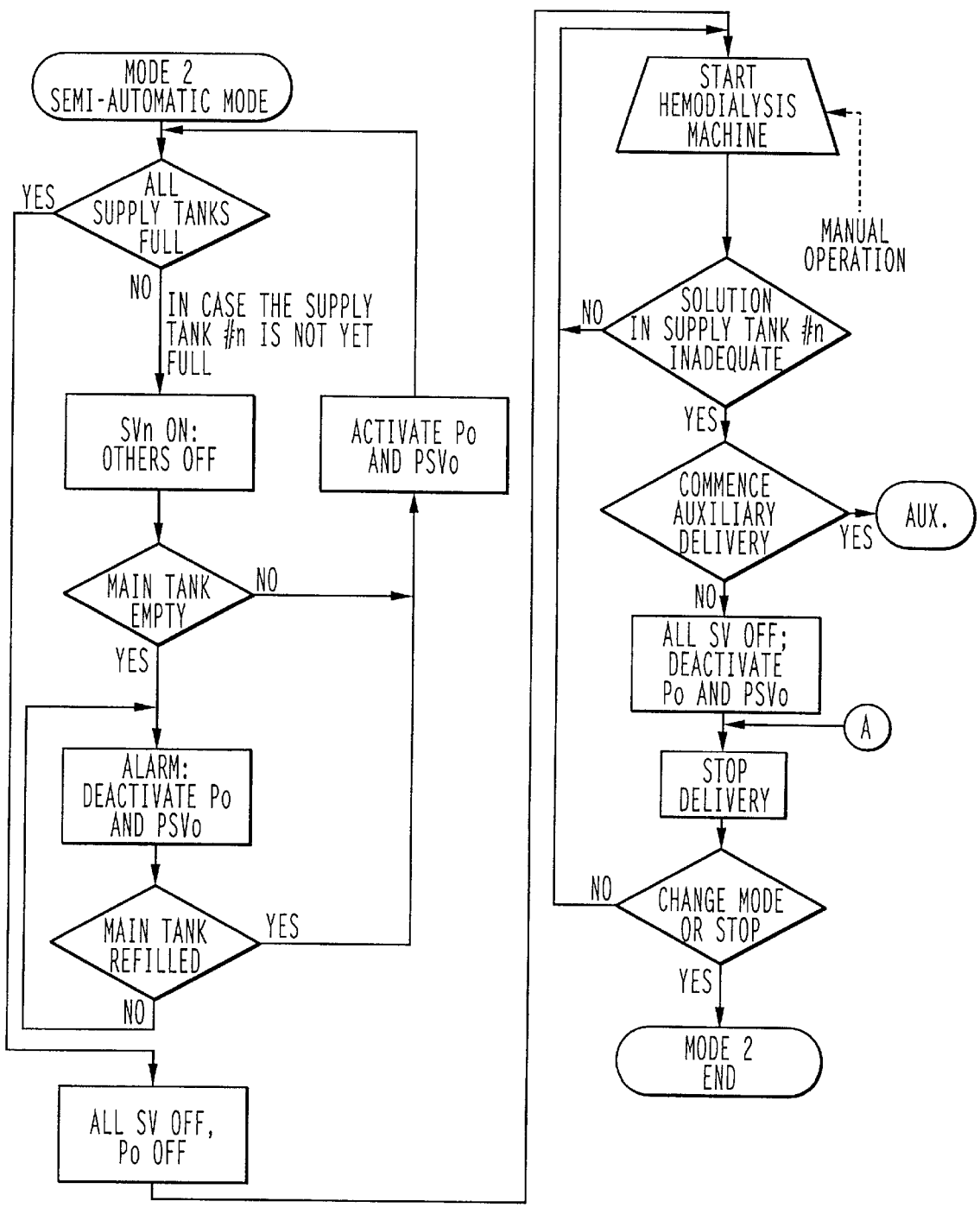
FIGS. 9A and 9B are flowcharts illustrating the operation of the preferred embodiment in a semi-automatic mode.
Figure 9B:
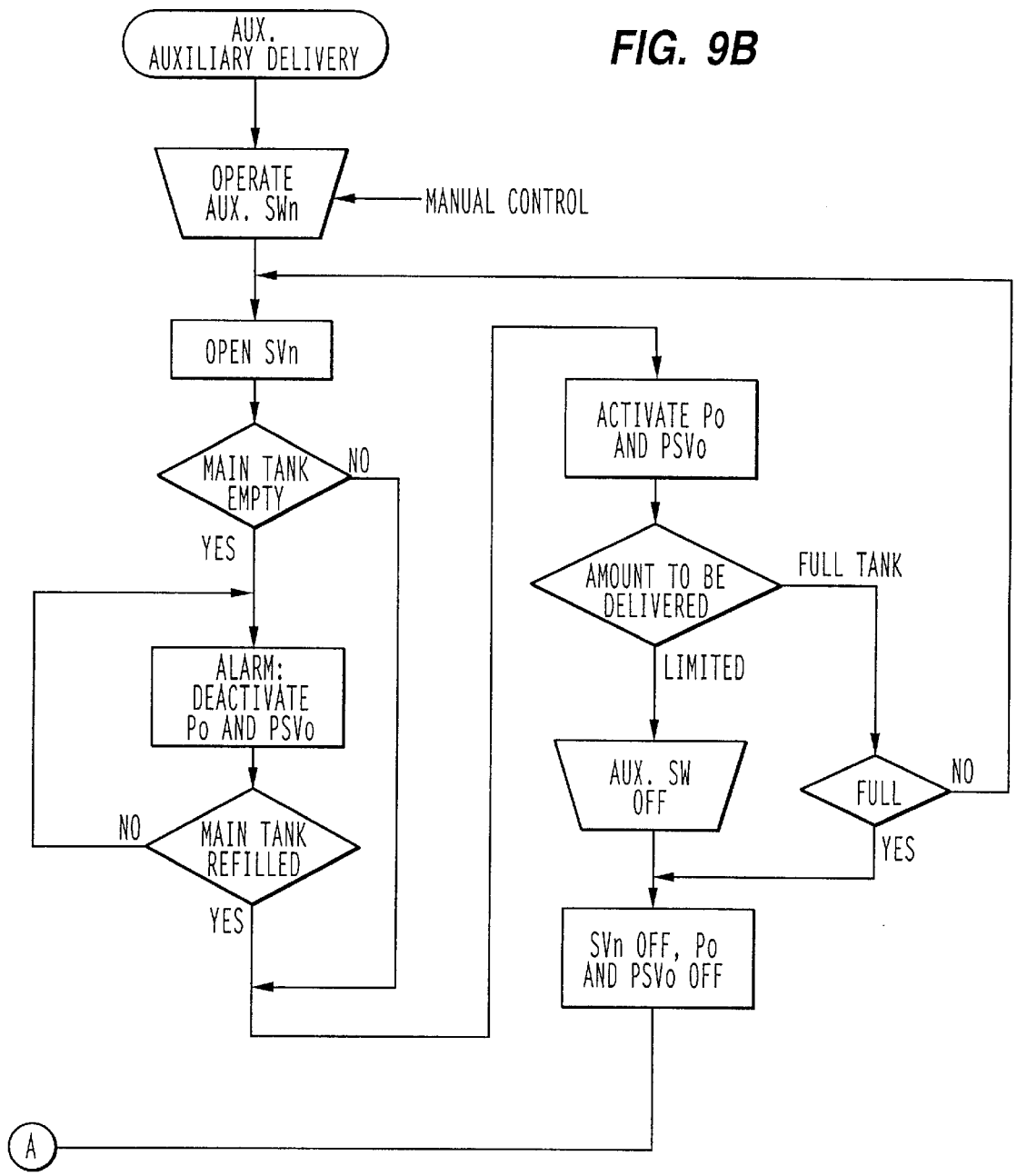

FIGS. 9A and 9B are flowcharts which illustrate the operation of the preferred embodiment in the semi-automatic mode. The initial operation in the semi-automatic mode is generally similar to that in the automatic mode. That is, each of the supply tanks 1 is filled with the hemodialysis solution once at the start of the operation in the semi-automatic mode. However, when the remaining amount of hemodialysis solution in any one of the supply tanks 1 becomes inadequate while the hemodialysis treatment has not yet ended, an auxiliary delivery operation is conducted, wherein the nurse operates a corresponding one of the switches AUX on the control panel 41 so as to open the associated electromagnetic valve SV and permit the addition of hemodialysis solution to the inadequate one of the supply tanks 1. The switch AUX is closed to stop the addition of hemodialysis solution. Operation of the preferred embodiment in the semi-automatic mode reduces wasting of the hemodialysis solution, thereby making the semi-automatic mode suitable for treatments during the final shift of the day.

Figure 10A:
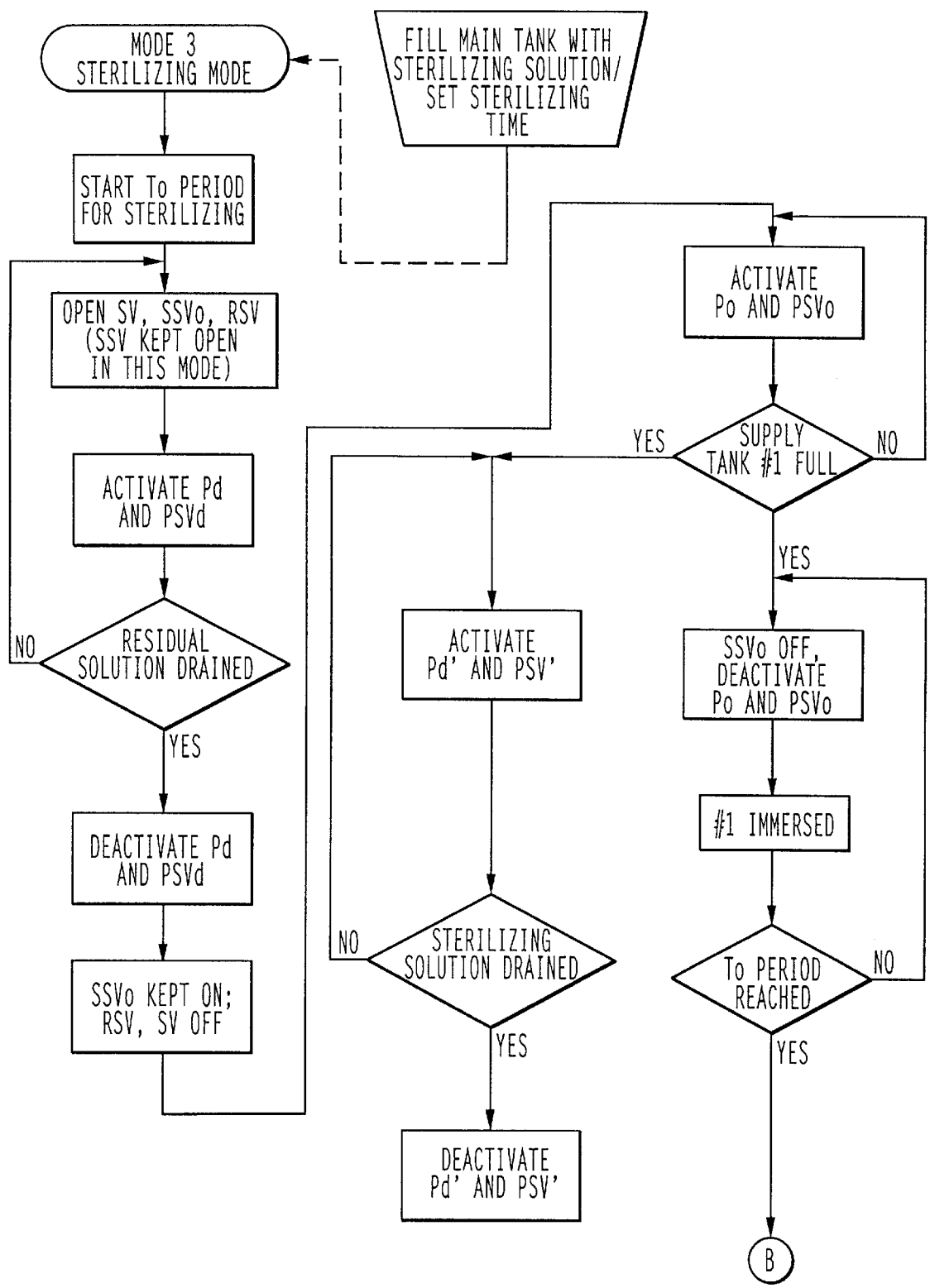
FIGS. 10A and 10B are flowcharts illustrating the operation of the preferred embodiment in a sterilizing mode.
Figure 10B:
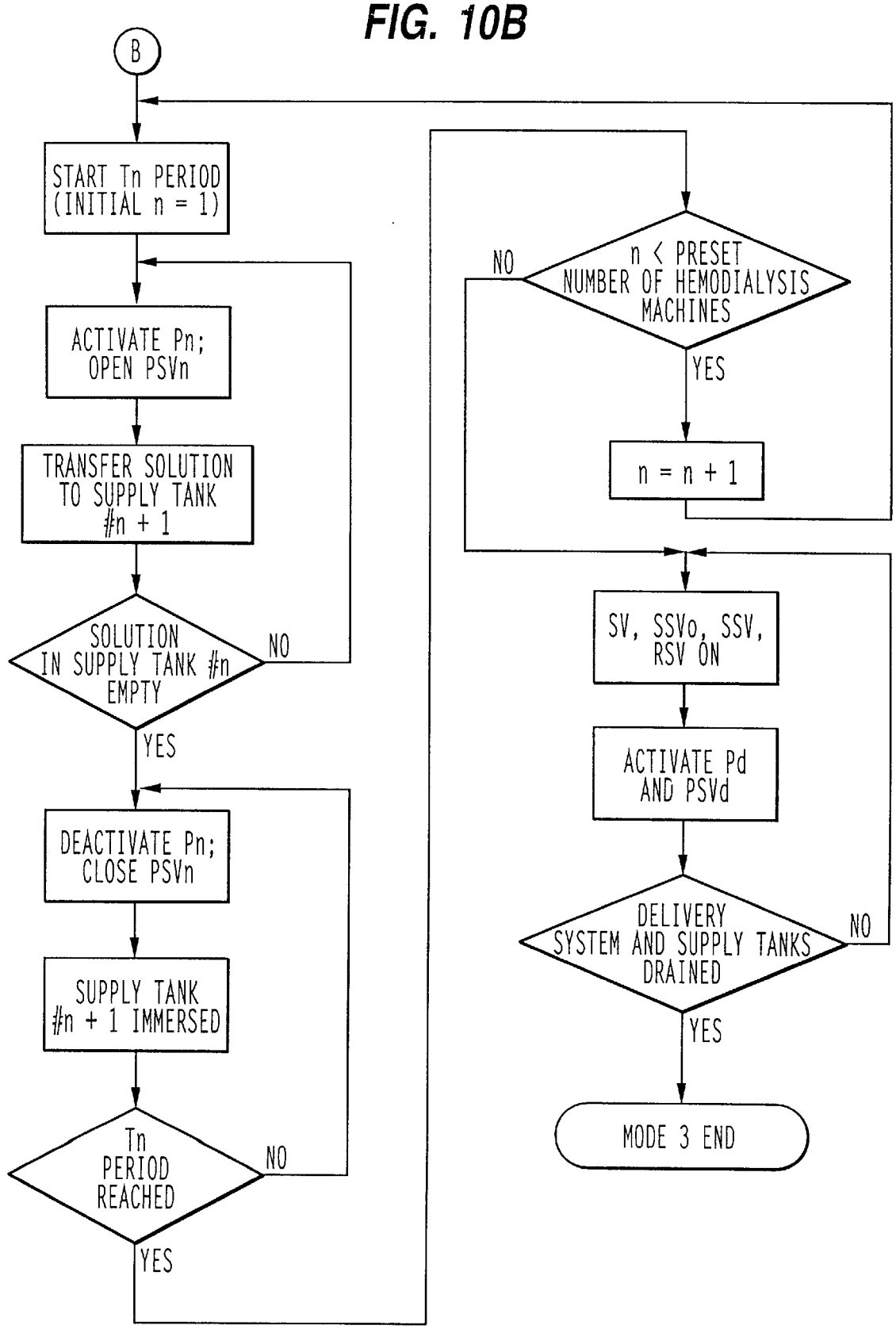

FIGS. 10A and 10B are flowcharts which illustrate the operation of the preferred embodiment in the sterilizing mode. Initially, the monitoring device 4 opens each electromagnetic valve SSV and detects whether residual hemodialysis solution is present in the solution delivery system 3 and in the supply tanks 1. A draining operation is performed automatically if residual hemodialysis solution is present. At this time, the drain pump Pd and the electromagnetic valve PSVd are activated, and the electromagnetic valves SV, RSV and SSVo are opened. The residual hemodialysis solution in the supply tanks 1 then flows through the corresponding electromagnetic valve SV and the drain pump Pd, as shown in FIG. 1. The draining operation is continued until all residual hemodialysis solution has been drained, i.e. the level sensing units 12 in the supply tanks 1 and the liquid sensing unit 306 in the main delivery pipe 30 are no longer in contact with the hemodialysis solution. To terminate the draining operation, the drain pump Pd and the electromagnetic valve PSVd are deactivated. The electromagnetic valves SSVo and SSV are kept open whilst the electromagnetic valves SV, RSV are closed at this time.

At the end of the draining operation, the central control circuit 40 starts counting to a preset desired sterilizing time. The delivery pump Po and the electromagnetic valve PSVo are activated so that sterilizing solution in the main tank 2 flows through the electromagnetic valve PSVo, the delivery pump Po, the electromagnetic valve SSVo and into the first supply tank 1. When the first supply tank 1 is filled with the sterilizing solution, the delivery pump Po and the electromagnetic valve PSVo are deactivated, and the electromagnetic valve SSVo is closed. The drain pump Pd' and the electromagnetic valve PSV' are activated so as to drain the remaining sterilizing solution in the main tank 2 via the drain pipe 32. After the first supply tank 1 has been immersed in the sterilizing solution for the preset sterilizing time, counting of the preset sterilizing time for the succeeding second supply tank 1 begins. At this time, the sterilizing solution in the first supply tank 1 is transferred to the second supply tank 1 via the first electromagnetic valve PSV, the first mediating pump P and the first electromagnetic valve SSV until the first supply tank 1 is completely drained, that is, the level sensing unit 12 in the first supply tank 1 is no longer in contact with the sterilizing solution. Both the first mediating pump P and the first electromagnetic valve PSV are deactivated at this time. The same procedure is repeated in series from the third up to the last supply tank 1. After the last supply tank 1 has been sterilized, the draining operation is performed once more to drain the sterilizing solution from the apparatus of this invention. In the preferred embodiment, the sterilizing time for each supply tank 1 may be set to 2 minutes, 3 minutes, 5 minutes or 10 minutes.

Figure 11:
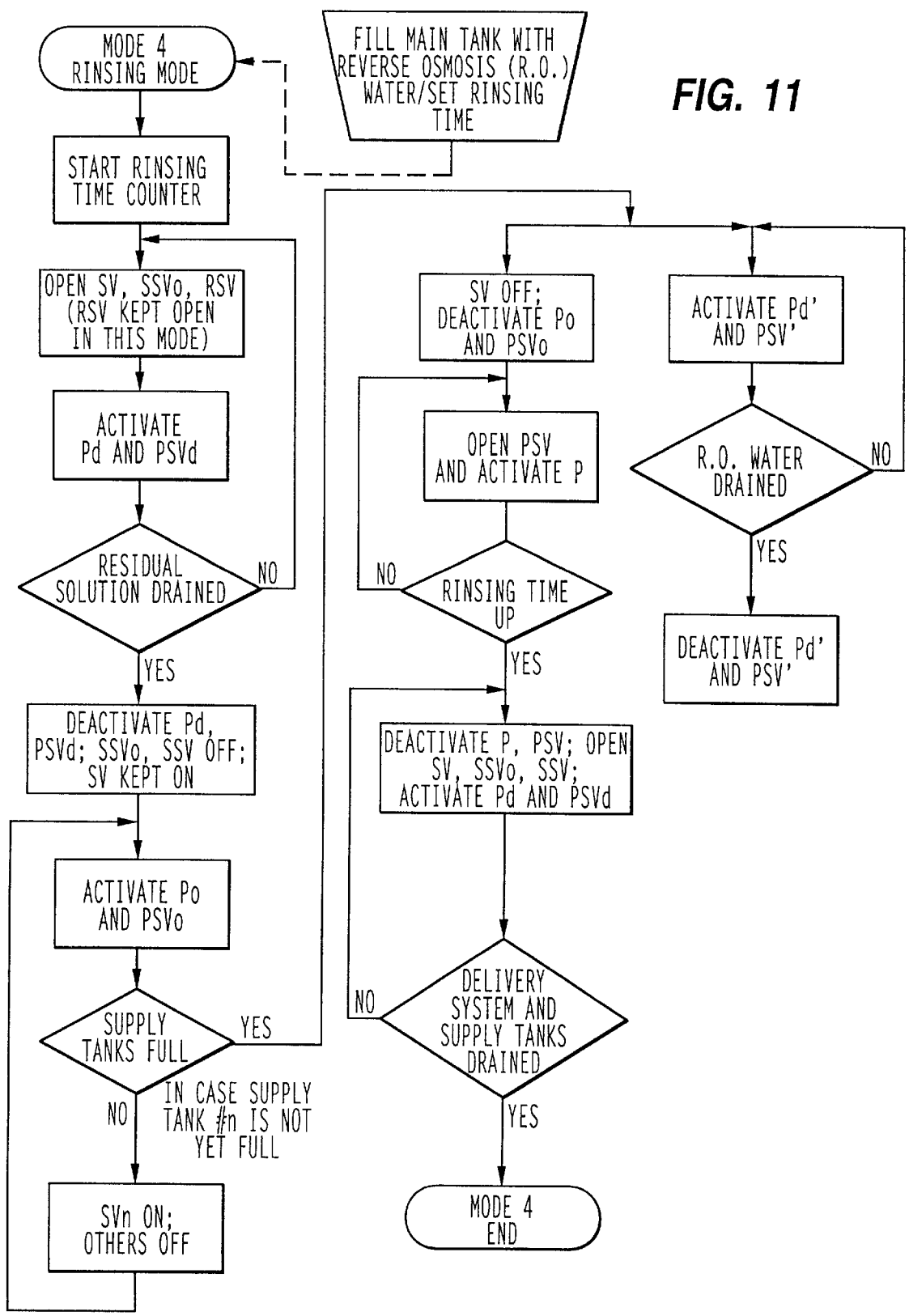
FIG. 11 is a flowchart illustrating the operation of the preferred embodiment in a rinsing mode.

FIG. 11 is a flowchart illustrating the operation of the preferred embodiment in the rinsing mode. Initially, the monitoring device 4 starts counting to the preset rinsing time. The electromagnetic valves RSV are always opened in this mode, and the monitoring device 4 determines whether there is residual hemodialysis solution present in the solution delivery system 3 and in the supply tanks 1. If any residual solution is present, a draining operation similar to that described beforehand is performed. After all residual hemodialysis solution has been drained, the drain pump Pd and the electromagnetic valve PSVd are deactivated, and the electromagnetic valves SSVo and SSV are closed. The reverse osmosis water in the main tank 2 is then delivered to the supply tanks 1 in a manner similar to the delivery of the hemodialysis solution during operation of the preferred embodiment in the automatic mode. Thus, the reverse osmosis water in the main tank 2 is delivered to the supply tanks 1 via the electromagnetic valve PSVo, the delivery pump Po and the main branch valves SV, as shown in FIG. 1. The main branch valves SV are closed after the respective supply tank 1 has been filled. When all of the supply tanks 1 are filled with the reverse osmosis water, the delivery pump Po and the electromagnetic valve PSVo are deactivated. Meanwhile, the drain pump Pd' and the electromagnetic valve PSV' are activated so as to drain the remaining solution in the main tank 2 via the drain pipe 32. The mediating pumps P and the electromagnetic valves PSV are activated to cause the solution in the supply tanks 1 to flow through the connecting port 10, the electromagnetic valve PSV, the mediating pump P, the electromagnetic valve RSV and back to the supply tanks 1 via the circulating port 11, thereby rinsing the interior of the supply tanks 1. When the monitoring device 4 has counted to the preset rinsing time, thereby signaling the end of the rinsing operation, the mediating pumps P and the electromagnetic valves PSV are deactivated, while the electromagnetic valves SV, SSV, RSV are opened, and the drain pump Pd and the electromagnetic valve PSVd are activated. Another draining operation is performed at this time to drain the reverse osmosis water from the apparatus of this invention. In the preferred embodiment, the supply tanks 1 are rinsed simultaneously, and the rinsing operation may be set to 5 minutes, 10 minutes, 15 minutes or 20 minutes.

In the preferred embodiment, with a series of built-in controlling processes, the central control circuit 40 is formed from logic circuits although a programmable logic array or a single-chip programmable microprocessor may be used instead. In designing the programmable logic array, the Boolean logic of the central control circuit 40 is obtained and is encoded for programming of the logic array. In the design of the microprocessor, the operation of the central control circuit 40 in the different modes is encoded into a series of program instructions which are then stored in the microprocessor.

It has thus been shown that the apparatus of the present invention can minimize human involvement in its various operations so as to result in effective use of time and manpower. In addition, when the monitoring device 4 is out of order, the delivery of hemodialysis solution can still be performed in the conventional manner. Moreover, in order to satisfy the user's demands, the monitoring device 4 can be expanded indefinitely to match the increase in the number of hemodialysis machines.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

I claim:

1. An apparatus for automatically delivering hemodialysis solution to a plurality of hemodialysis machines, comprising:
   a plurality of supply tanks adapted to be fluidly communicated with a corresponding one of the hemodialysis machines, each of said supply tanks having a bottom portion provided with a connecting port, an upper level sensing unit for detecting whether said supply tank is full, and a lower level sensing unit for detecting whether said supply tank is empty;
   a main tank for containing hemodialysis solution therein, said main tank having an outlet port;
   a solution delivery system including
      a main delivery pipe having a terminal portion and an inlet section connected to said outlet port of said main tank,
      an electromagnetic delivery control valve provided on said main delivery pipe;
      a delivery pump provided on said main delivery pipe;
      a plurality of main branch pipes, each of said main branch pipes having an input portion connected fluidly to said main delivery pipe and an output portion connected fluidly to said connecting port of a respective one of said supply tanks, each of said main branch pipes being provided with an electromagnetic main branch valve,
      a secondary pipe connected fluidly to said inlet section of said main delivery pipe and to said output portion of each of said main branch pipes, and
      a bypass pipe connected between said terminal portion of said main delivery pipe and said secondary pipe; and
   a monitoring device connected electrically to said upper and lower level sensing units, said delivery control valve, said delivery pump and said main branch valves, said monitoring device being operable in an automatic mode, wherein said monitoring device activates and deactivates said delivery control valve, said delivery pump and said main branch valves to fill up said supply tanks.

2. The apparatus as claimed in claim 1, wherein said solution delivery system further comprises a pressure regulator provided on said inlet section of said main delivery pipe downstream of said delivery pump.

3. The apparatus as claimed in claim 1, wherein said solution delivery system further comprises a filter unit provided on said inlet section of said main delivery pipe downstream of said delivery pump.

4. The apparatus as claimed in claims 1, wherein said bypass pipe is provided with a pressure relief valve.

5. The apparatus as claimed in claim 1, wherein said main tank is provided with a remainder sensing unit to detect whether said main tank is empty, said remainder sensing unit being connected electrically to said monitoring device.

6. The apparatus as claimed in claim 1, wherein said solution delivery system further comprises:
   an electromagnetic sterilization entrance valve provided on an inlet portion of said secondary pipe; and
   a plurality of electromagnetic mediating pump control valves, a plurality of mediating pumps, and a plurality of transmission control valves provided on said secondary pipe;
   said secondary pipe having a plurality of pipe sections disposed between a respective pair of said main branch pipes and provided with one of said mediating pump control valves, one of said mediating pumps and one of said transmission control valves;
   each of said sterilization entrance valve, said mediating pump control valves, said mediating pumps and said transmission control valves being connected electrically to and controlled by said monitoring device to permit supply of sterilizing solution to one of said supply tanks and to transfer the sterilizing solution in said one of said supply tanks to an adjacent one of said supply tanks when said monitoring device is operated in a sterilizing mode.

7. The apparatus as claimed in claim 6, wherein said bypass pipe is provided with a pressure relief valve.

8. The apparatus as claimed in claim 6, wherein:

each of said supply tanks has a top portion provided with a circulating port; and said solution delivery system further comprises a plurality of secondary branch pipes, each of which is connected fluidly to fluid leaving an outlet port of a respective one of said mediating pumps and to fluid entering said circulating port of a respective one of said supply tanks, each of said secondary branch pipes being provided with an electromagnetic circulation control valve connected electrically to said monitoring device;

said circulation control valves, said sterilization entrance valve, said mediating pump control valves, said mediating pumps and said transmission control valves being controlled by said monitoring device to permit supply of rinsing water to said supply tanks and to circulate the rinsing water in said supply tanks via said main branch pipes, said pipe sections of said secondary pipe, and said secondary branch pipes when said monitoring device is operated in a rinsing mode.

9. The apparatus as claimed in claim 8, wherein said bypass pipe is provided with a pressure relief valve.

10. An apparatus for automatically delivering hemodialysis solution to a plurality of hemodialysis machines, comprising:

a plurality of supply tanks adapted to be fluidly communicated with a corresponding one of the hemodialysis machines, each of said supply tanks having a bottom portion provided with a connecting port, an upper level sensing unit for detecting whether said supply tan is full, and a lower level sensing unit for detecting whether said supply tank is empty;

a main tank for containing hemodialysis solution therein, said main tank having an outlet port;

a solution delivery system including a main delivery pipe having an inlet section connected to said outlet port of said main tank, an electromagnetic delivery control valve provided on said main delivery pipe, a delivery pump provided on said main delivery pipe, and a plurality of main branch pipes, each of said main branch pipes having an input portion connected fluidly to said main delivery pipe and an output portion connected fluidly to said connecting port of a respective one of said supply tanks, each of said main branch pipes being provided with an electromagnetic main branch valve, and a drain pipe connected fluidly to said main tank and provided with a drain pump and an electromagnetic drain valve; and a monitoring device connected electrically to said upper and lower level sensing units, said delivery control valve, said delivery pump, said main branch valves, said drain pump and said electromagnetic drain valve, said monitoring device being operable in an automatic mode, wherein said monitoring device activates and deactivates said delivery control valve, said delivery pump and said main branch valves to fill up said supply tanks, and wherein said monitoring device activates and deactivates said drain pump and said electromagnetic drain valve to drain said main tank.

11. The apparatus as claimed in claim 10, wherein said drain pipe is further provided with a bypass valve.

12. An apparatus for automatically delivering hemodialysis solution to a plurality of hemodialysis machines, comprising:

a plurality of supply tanks adapted to be fluidly communicated with a corresponding one of the hemodialysis machines, each of said supply tanks having a bottom portion provided with a connecting port, an upper level sensing unit for detecting whether said supply tank is full, and a lower level sensing unit for detecting whether said supply tank is empty;

a main tank for containing hemodialysis solution therein, said main tank having an outlet port;

a solution delivery system including a main delivery pipe having an inlet section connected to said outlet port of said main tank and a distal section provided with a residual sensing unit to detect whether residual solution is present therein, an electromagnetic delivery control valve provided on said main delivery pipe, a delivery pump provided on said main delivery pipe, a plurality of main branch pipes, each of said main branch pipes having an input portion connected fluidly to said main delivery pipe and an output portion connected fluidly to said connecting port of a respective one of said supply tanks, each of said main branch pipes being provided with an electromagnetic main branch valve, a drain pump provided on said main delivery pipe, and an electromagnetic draining control valve provided on said main delivery pipe; and a monitoring device connected electrically to said upper and lower level sensing units, said delivery control valve, said delivery pump, said main branch valves, said residual sensing unit, said drain pump and said draining control valve, said monitoring device being operable in an automatic mode, wherein said monitoring device activates and deactivates said delivery control valve, said delivery pump and said main branch valves to fill up said supply tanks, and wherein said monitoring device activates and deactivates said drain pump and said draining control valve to drain said main delivery pipe of residual solution.

* * * * *